United States Patent [19]

Schmerling

[11] 4,009,203
[45] Feb. 22, 1977

[54] CONVERSION OF OLEFINS TO ESTERS

[75] Inventor: Louis Schmerling, Riverside, Ill.

[73] Assignee: Universal Oil Products Company, Des Plaines, Ill.

[22] Filed: Jan. 27, 1975

[21] Appl. No.: 544,595

[52] U.S. Cl. .................... 260/497 R; 260/410.9 R; 260/476 R; 260/485 R; 260/486 R; 260/487
[51] Int. Cl.² ........................................ C07C 67/04
[58] Field of Search ............... 260/497 R, 410.9 R, 260/486 R, 487, 476 R, 485 R

[56] References Cited
UNITED STATES PATENTS

| 2,598,263 | 5/1952 | Johnson et al. | 260/497 R |
| 3,649,655 | 3/1972 | Selwitz | 260/497 R |
| 3,907,873 | 9/1975 | Wight et al. | 260/497 R |

OTHER PUBLICATIONS

Guenzet, Tetrahedron Letters, 26, (1972) pp. 2647–2650.

*Primary Examiner*—Anton H. Sutto
*Assistant Examiner*—Michael Shippen
*Attorney, Agent, or Firm*—James R. Hoatson, Jr.; Raymond H. Nelson; William H. Page, II

[57] ABSTRACT

Olefins, and particularly olefinic hydrocarbons, may be converted to esters by treating the olefin with a carboxylic acid in the presence of a catalyst comprising the product resulting from the reaction of a tin halide with a carboxylic acid, the conversion taking place at temperatures ranging from ambient to about 150° C.

10 Claims, No Drawings

CONVERSION OF OLEFINS TO ESTERS

This invention relates to a process for the conversion of olefins. More specifically, the invention is concerned with a process whereby olefins are treated with a carboxylic acid in the presence of a catalyst comprising the product resulting from the reaction of a tin halide with a carboxylic acid (namely a trihalostannic salt of the acid) to form reaction products predominantly in the form of esters.

Heretofore, when olefins have been treated with a carboxylic acid in the presence of a tin halide, the reaction product resulting from this treatment comprises a mixture of a hydrohalide and an ester in no less than about 1:3 molar quantity. However, in many instances, it is desirable to obtain esters rather than the hydrohalides due to the fact that the esters will find a wider variety of uses in the chemical field. For example, butyl acetates which may be prepared according to this process and which will comprise sec-butyl acetate or t-butyl acetate may be used as solvents for lacquers, lacquer enamels, perfumes, flavoring extracts, natural gums and synthetic resins, nitrocellulose, celluloid products, artificial leather, plastic, wood or as an antiknock agent for gasoline, etc.; hexyl acetates are useful as solvents for cellulose esters and resins; heptyl formate may be used in artificial fruit essances and octyl acetate will find use in perfumery and flavors. In contradistinction to this, the hydrohalides, while useful, will not find such a wide variety of uses nor will the monetary return from these products be as great as will be received from the esters.

In order to obtain a greater yield of the desired esters, it has now been discovered that by treating the olefin with a carboxylic acid in the presence of the product resulting from the prior reaction between the tin halide and the carboxylic acid, it is possible to markedly decrease the relative yields of the less desirable hydrohalides while increasing the yield of the desired esters.

It is therefore an object of this invention to provide a process for converting olefins.

A further object of this invention is to provide a process for converting olefins to desired products such as esters.

In one aspect an embodiment of this invention resides in a process for converting an olefin to an ester which comprises treating said olefin at reaction conditions with a carboxylic acid in the presence of a catalyst comprising the product resulting from the reaction of a tin halide with a carboxylic acid, and recovering the resultant ester.

A specific embodiment of this invention is found in a process for converting an olefin to an ester which comprises treating 7-tetradecene with propionic acid at a temperature in the range of from ambient to about 150° C. with the product resulting from the reaction of stannic chloride with propionic acid, and recovering the resultant tetradecyl propionate.

Other objects and embodiments will be found in the following further detailed description of the present invention.

As hereinbefore set forth, the present invention is concerned with a process for the conversion of olefins, and particularly to an improvement in the conversion process whereby the desired product will comprise principally an ester of the olefin rather than a mixture of the ester and a relatively great amount of an alkyl halide. In order to obtain the objective of preparing a larger percentage of olefins with the concurrent smaller percentage of hydrohalide being produced, it has now been discovered that the olefin may be treated with a carboxylic acid in the presence of a catalyst comprising the product resulting from the reaction of a tin halide with a carboxylic acid (usually the one which is to be used to esterify the olefin) prior to treating said olefin. This objective may be attained by reacting a catalytic amount of a tin halide with a carboxylic acid at temperatures ranging from about 50° to about 200° C. and preferably in a range of from about 100° to about 130° C. for a period of time ranging from about 0.5 up to about 20 hours or more in duration. Another variable which may be utilized is that of pressure. In the preferred embodiment, the pressure which is utilized is atmospheric, although superatmospheric pressures ranging up to about 100 atmospheres may be employed. When employing these superatmospheric pressures, the degree of temperatures which is necessary to effect the reaction may be lowered and, in addition, the residence time may also be shortened. It is to be understood that the various parameters of time, temperature and pressure will be dependent, to a large extent, upon the particular tin halide and particular carboxylic acid which are undergoing reaction.

Examples of tin halides which may be employed will preferably comprise a halide of tin in which the tin is present in its highest valence state, specific examples of these compounds being stannic chloride, stannic bromide, stannic iodide, etc., the preferred halide, due to its greater availability and activity comprising stannic chloride and preferably in an anhydrous form.

The aforesaid tin halide is reacted with the carboxylic acid which is to form one component of the ester. The term "carboxylic acid" as used in the present specification and appended claims will refer to aliphatic, aromatic, alkenic and halogenated aliphatic and aromatic acids. Suitable carboxylic acids which may be employed in the reaction with the stannic chloride will include the fatty acids containing from 1 to about 20 carbon atoms in length such as formic acid, acetic acid, propionic acid, butyric acid, valeric acid, caproic acid, enanthylic acid, caprylic acid, pelargonic acid, capric acid, undecylic acid, lauric acid, tridecoic acid, myristic acid, pentadecanoic acid, palmitic acid, margaric acid, stearic acid, arachidic acid, etc.; or aromatic acids such as benzoic acid, phenylacetic acid, phenylpropionic acid, phenylbutyric acid, phenylvaleric acid, o-toluic acid, m-toluic acid, p-toluic acid, the isomeric xylic acids, the isomeric trimethylbenzoic acids, etc. As in the case of the aforementioned olefins, the carboxylic acids hereinbefore set forth are only representative of the class of acids which may be used and that the present invention is not necessarily limited thereto.

It is also contemplated within the scope of this invention that other carboxylic acids such as unsaturated acids including acrylic acid, crotonic acid, isocrotonic acid, methacrylic acid, tiglic acid, angelic acid, senecioic acid, oleic acid, etc., or dibasic acids such as oxalic acid, malonic acid, succinic acid, glutaric acid, adipic acid, pimelic acid, suberic acid, azelaic acid, sebasic acid, fumaric acid, maleic acid, glutaconic acid, etc., or halogenated aliphatic acids containing from 2 to about 20 carbon atoms such as monochloroacetic acid, dichloroacetic acid, trichloroacetic acid, monobromoacetic acid, dibromoacetic acid, tribromoacetic acid, monochloropropionic acid, dichloropropionic acid, trichloropropionic acid, monobromopropionic acid, dibromopropionic acid, tribromopropionic acid, monochlorobutyric acid, dichlorobutyric acid, trichlorobutyric acid, monobromobutyric acid, dibromobutyric acid, tribromobutyric acid, monochlorovaleric acid, dichlorovaleric acid, trichlorovaleric acid, monobromovaleric acid, dibromovaleric acid, tribromovaleric acid, monochlorocaproic acid, dichlorocaproic acid, trichlorocaproic acid, monobromocaproic acid, dibromocaproic acid, tribromocaproic acid, the corresponding mono and polychloro and bromo-substituted heptanoic acids, caprylic acids, pelargonic acids, capric acids, undecylic acid, dodecylic acid, tridecylic acid, tetradecylic acid, pentadecylic acid, hexadecylic acid, heptadecylic acid, octadecylic acid, nonadecylic acid, eicosic acid, etc., may also be used.

The product which results from the reaction between the aforementioned tin halide and carboxylic acid is then utilized as the catalyst in the reaction between a carboxylic acid with an olefin, either an alkene or a cycloalkene. Some specific examples of olefins which may be converted to esters by treatment with the product resulting from the reaction between a tin halide and a carboxylic acid according to the process of the present invention will comprise those compounds containing from 4 to about 20 and preferably from about 8 to about 20 carbon atoms such as alkenes, both straight and branch-chained including 1-butene, 2-butene, 1-pentene, 2-pentene, 1-hexene, 2-hexene, 3-hexene, 1-heptene, 2-heptene, 3-heptene, 1-octene, 2-octene, 3-octene, 4-octene, 1-nonene, 2-nonene, 3-nonene, 4-nonene, 1-decene, 2-decene, 3-decene, 4-decene, 5-decene, 1-undecene, 2-undecene, 3-undecene, 4-undecene, 5-undecene, 1-dodecene, 2-dodecene, 3-dodecene, 4-dodecene, 5-dodecene, 6-dodecene, 1-tetradecene, 2-tetradecene, 3-tetradecene, 4-tetradecene, 5-tetradecene, 6-tetradecene, 7-tetradecene, the isomeric pentadecenes, hexadecenes, heptadecenes, octadecenes, nonadecenes, eicosenes, 2-methylbutene-1, 2-methylbutene-3, 2-methylpentene-1, 2-methylpentene-3, 2-methylpentene-4, 3-methylpentene-1, 3-methylpentene-2, 3-methylhexene-1, 3-methylhexene-2, 3-methylhexene-5, 2-methylheptene-1, 2-methylheptene-2, 2-methylheptene-4, 2-methylheptene-6, the branch-chained isomeric octenes, nonenes, decenes, etc.; cycloalkenes containing from 5 to about 8 carbon atoms in the chain including cyclopentene, cyclohexene, cycloheptene, cyclooctene, 1-methyl-cyclopentene-1, 1-methylcyclohexene-1, 3-methylcyclohexene-1, 1-methyl-cycloheptene-1, 3-methylcycloheptene-1, 4-methylcycloheptene-1, 1-methyl-cyclooctene-1, 3-methylcyclooctene-1, 4-methylcyclooctene-1, etc. It is to be understood that the aforementioned olefinic hydrocarbons are only representative of the class of olefinic compounds which may be converted to esters and hydrohalides according to the process of this invention, and that said invention is not necessarily limited thereto.

The conversion of the olefin to an ester thereof by treatment with a carboxylic acid is effected at reaction conditions which include a temperature ranging from about ambient (20°–25° C.) up to about 150° C. or more and preferably in a range of from about 40° to about 125° C. It is also contemplated within the scope of this invention that the reaction is effected at atmospheric pressure. However, if so desired, superatmospheric pressures up to about 100 atmospheres may be employed in order to reduce the temperature which is required to effect the reaction and also to reduce the residence time. The aforesaid time which is required to effect the conversion may range from about 0.5 up to about 20 hours or more in duration, said residence time being dependent upon the various parameters of the reaction including temperature, pressure and reactants.

The process of this invention may be effected in any suitable manner and may comprise either a batch or continuous type operation. For example, when a batch type operation is used, a quantity of the reactants, namely, the olefinic hydrocarbon and the carboxylic acid as well as the catalyst comprising the product resulting from the reaction between a tin halide and a carboxylic acid at reaction conditions hereinbefore set forth, are placed in an appropriate apparatus which may comprise a flask or, if superatmospheric pressures are to be used, an autoclave of the rotating or mixing type. The reaction is allowed to proceed for a predetermined period of time at reaction conditions of temperature and pressure within the range hereinbefore set forth, at the end of which time heating is discontinued and the apparatus and contents thereof are allowed to cool to room temperature. The reaction mixture is recovered and subjected to conventional means of separation such as extraction, washing, fractional distillation, etc., whereby the desired products are recovered.

It is also contemplated within the scope of this invention that the process in which an olefin is converted to an ester by treatment with a carboxylic acid in the presence of a catalyst comprising the product resulting from the reaction between a tin halide and a carboxylic acid may be effected in a continuous manner of operation. When such a type of operation is used, the starting materials comprising the olefin, the carboxylic acid and the aforementioned reaction product are continuously charged to a reaction zone which is maintained at the proper operating conditions of temperature and pressure. Upon completion of the desired residence time, the reactor effluent is continuously withdrawn and subjected to conventional means of separation similar in nature to those hereinbefore set forth whereby the desired reaction product comprising the ester is separated and recovered while any unreacted starting materials may be recycled to the reaction zone to form a portion of the feed stock.

The following examples are given to illustrate the process of the present invention which, however, are not intended to limit the generally broad scope of the present invention in strict accordance therewith.

EXAMPLE I

To prepare the product resulting from the reaction of a tin halide with a carboxylic acid, 49 grams of propionic acid was heated with 25 grams of stannic chloride at a temperature in the range of from 85° to 140° C. for a period of 6 hours. At the end of this time heating was discontinued and the product was recovered, the yield being 61 grams of product comprising propionoxystannic trichloride.

To convert the olefin, 14 grams of 7-tetradecene, 40 grams of propionic acid and 31 grams of the reaction product hereinbefore prepared were placed in the glass liner of a rotating autoclave. The liner was sealed into the autoclave and a sufficient amount of nitrogen pressed in until an initial operating pressure of 30 atmospheres was reached. The autoclave was then rotated and heated to a temperature of 100° C. for a period of 4 hours, the maximum pressure during this time rising to 43 atmospheres. At the end of the 4-hour period, heating was discontinued and the autoclave was allowed to return to room temperature, the final pressure at room temperature being 30 atmospheres. The excess pressure was discharged and the autoclave was opened, 85 grams of a clear dark amber liquid being recovered. The reaction product was analyzed by means of gas chromatography, said analysis disclosing the presence of tetradecyl chloride and tetradecyl propionate, the ratio of gas chromatography peak areas of unreacted olefin to tetradecyl chloride to tetradecyl propionate being 1.0:0.3:1.6.

When untreated stannic chloride was used as the catalyst under the same conditions, the ratio of products was 1.0:3.0:3.6.

EXAMPLE II

To again illustrate the advantage of using the product resulting from the reaction of a tin halide with a carboxylic acid as the catalyst for the reaction, another experiment was performed in which 22 grams of 7-tetradecene, 62 grams of propionic acid and 6 grams of stannic chloride were placed in the glass liner of a rotating autoclave. The autoclave was sealed and nitrogen pressed in until an initial pressure of 30 atmospheres was reached. Thereafter the autoclave was rotated and heated to a temperature of 140° C. for a period of 4 hours, the maximum pressure during this time reaching 49 atmospheres. At the end of the 4-hour period, heating was discontinued and the autoclave was allowed to return to room temperature. The excess pressure was discharged, the autoclave was opened and the reaction product comprising 89 grams of a dark amber liquid was recovered. Analysis of the product by means of gas-liquid chromatography showed a ratio of unreacted olefin (7-tetradecene) to tetradecyl chloride to tetradecyl propionate of 1.0:0.4:1.0.

It is therefore apparent from a comparison of the products recovered from the experiments that the use of a product resulting from the reaction of stannic chloride and propionic acid as a catalyst for the reaction gave a higher ratio of ester to chloride than did the use of stannic chloride alone as a catalyst.

EXAMPLE III

In this example the catalyst was prepared by heating a solution of 32 grams of stannic chloride in 52 grams of acetic acid in a flask at a temperature in the range of from 123° to 126° C. for a period of 1.5 hours.

Following this, 26 grams (0.13 mole) of 7-tetradecene, 51 grams (0.69 mole) of acetic acid and 28 grams of a solution of the catalyst (containing about 0.05 mole of tin salt) prepared according to the above paragraph were placed in the glass liner of a rotating autoclave. The liner was sealed into the autoclave and nitrogen pressed in until an initial pressure of 30 atmospheres was reached. The autoclave was then rotated and heated to a temperature of 100° C., being maintained at this temperature for a period of 4 hours. During this time, the maximum pressure rose to 43 atmospheres. At the end of the 4-hour period, heating was discontinued and the autoclave was allowed to return to room temperature. The excess pressure was discharged and the autoclave was opened, 104 grams of dark amber liquid product being recovered therefrom. The reaction product was analyzed by means of gas-liquid chromatography, the results showing that the ratio of unreacted 7-tetradecene to tetradecyl chloride to tetradecyl acetate was 1.0:0.5:1.6.

In a similar experiment the catalyst was prepared by refluxing a solution of 27 grams of stannic chloride in 121 grams of acetic acid at a temperature of 125° C. for a period of 1.5 hours, during which time 3 grams of hydrogen chloride was evolved.

The olefin was converted by treating 20 grams (0.10 mole) of 7-tetradecene with 10 grams (0.17 mole) of acetic acid in the presence of 60 grams of the catalyst solution which was prepared in the above paragraph. The reaction was effected in a rotating autoclave under an initial pressure of 30 atmospheres of nitrogen at a temperature of 100° C. for a period of 4 hours. During the 4-hour period, the maximum pressure which was reached was 43 atmospheres, said pressure dropping to 30 atmospheres when the autoclave was allowed to return to room temperature. Upon discharge of the pressure and opening the autoclave, 91 grams of a dark brown liquid was recovered. Gas-liquid chromatographic analysis of the product disclosed that the chief reaction products comprised tetradecyl chloride and tetradecyl acetate. The ratio of unreacted 7-tetradecene to tetradecyl chloride to tetradecyl acetate was 1.0:0.2:1.2.

A similar experiment in which smaller amounts of stannic chloride and acetic acid were refluxed at 120° C. for 3 hours with the evolution of hydrogen chloride resulted in the obtention of a product which, upon analysis, showed that the ratio of unreacted 7-tetradecene to tetradecyl chloride to tetradecyl acetate was 1.0:0.1:0.8.

It is therefore apparent from the above three experiments that by utilizing a catalyst comprising the product resulting from the reaction between stannic chloride and acetic acid prior to treatment of 7-tetradecene with acetic acid, resulted in a product in which the ester, namely, tetradecyl acetate, was present in a greater amount over the tetradecyl chloride than would ordinarily be obtained when utilizing only stannic chloride as the catalyst.

EXAMPLE IV

In this example 105 grams (1.75 mole) of acetic acid and 30 grams of a catalyst which is prepared by refluxing a solution of stannic bromide in acetic acid at a temperature of 125° C. for a period of 3 hours are placed in the glass liner of a rotating autoclave which is thereafter sealed. Isobutylene (25 grams, 0.54 mole) is pressed in followed by nitrogen which is pressed in until an initial pressure of 30 atmospheres is reached and the autoclave is then heated to a temperature of 100° C. for a period of 4 hours. At the end of the 4-hour period, heating is discontinued and the autoclave is allowed to return to room temperature. The final pressure which is 30 atmospheres is discharged and the autoclave is opened. The liquid product which is recovered is subjected to gas-liquid chromatographic analysis which will disclose that the chief products comprise t-butyl chloride and t-butyl acetate, the t-butyl acetate being present in a relatively greater amount over the t-butyl chloride than will be present when only stannic bromide is utilized as the catalyst.

EXAMPLE V

In like manner, 47 grams (0.57 mole) of cyclohexene, 73 grams (0.99 mole) of propionic acid and 30 grams of a catalyst which is prepared by refluxing a solution of stannic chloride in propionic acid for a period of 3 hours at a temperature of 125°–145° C. are placed in the glass liner of a rotating autoclave. The autoclave is sealed and 30 atmospheres of nitrogen is pressed in. The autoclave is then heated to a temperature of 100° C. and maintained thereat for a period of 4 hours, during which time the maximum pressure will rise to about 45 atmospheres. At the end of the 4-hour period, heating is discontinued and the autoclave is allowed to return to room temperature, the final pressure at room temperature being 30 atmospheres. The excess pressure is discharged and the autoclave is opened, the dark amber liquid comprising the reaction product being recovered therefrom. The product is then subjected to gas-liquid chromatographic analysis which will disclose the chief products to be cyclohexyl chloride and cyclohexyl propionate, said ester being present in a greater amount in relation to the chloride than will be found when only stannic chloride is used as the catalyst.

EXAMPLE VI

In this example 55 grams (0.49 mole) of 1-octene, 48 grams (0.46 mole) of formic acid and 15 grams of a catalyst which is prepared by refluxing a solution of stannic chloride in formic acid for a period of 3 hours prior to use thereof are placed in a flask with a magnetic bar utilized to stir the reactants. The flask is then heated to a temperature of 60° C. and maintained in a range of from 60°–65° C. for a period of 1.5 hours. At the end of this time, heating is discontinued and the flask is allowed to return to room temperature. The product is recovered and subjected to gas-liquid chromatographic analysis which discloses the chief products to be sec-octyl chlorides and sec-octyl formates, the octyl formates being present in a greater amount in relation to the octyl chlorides than is obtained when utilizing only stannic chloride as the catalyst.

I claim as my invention:

1. A process for the production of an ester which comprises reacting an olefinic hydrocarbon with a carboxylic acid selected from the group consisting of aliphatic, aromatic, alkenic and halogenated aliphatic and aromatic acids in the presence of the pre-formed acyloxystannic trihalide reaction product of a tin halide selected from the group consisting of stannic chloride, bromide and iodide with a carboxylic acid selected from the group consisting of aliphatic, aromatic, alkenic and halogenated aliphatic and aromatic acids, and recovering the resultant ester.

2. The process of claim 1 in which the first-mentioned acid and the second-mentioned acid are the same.

3. The process as set forth in claim 1 in which said reaction is effected at a temperature in the range of from about ambient to about 150° C. and a pressure in the range of from atmospheric to about 100 atmospheres.

4. The process as set forth in claim 1 in which said tin halide is stannic chloride.

5. The process as set forth in claim 1 in which the reaction of the tin halide with the carboxylic acid is effected at a temperature in the range of from about 50° to about 200° C.

6. The process as set forth in claim 2 in which said olefinic hydrocarbon is 7-tetradecene, said tin halide is stannic chloride, said carboxylic acid is propionic acid and said ester is tetradecyl propionate.

7. The process as set forth in claim 2 in which said olefinic hydrocarbon is 7-tetradecene, said tin halide is stannic chloride, said carboxylic acid is acetic acid and said ester is tetradecyl acetate.

8. The process as set forth in claim 2 in which said olefinic hydrocarbon is cyclohexene, said tin halide is stannic chloride, said carboxylic acid is acetic acid and said ester is cyclohexyl acetate.

9. The process as set forth in claim 2 in which said olefinic hydrocarbon is 1-octene, said tin halide is stannic chloride, said carboxylic acid is formic acid and said ester is sec-octyl formate.

10. The process as set forth in claim 2 in which said olefinic hydrocarbon is isobutylene, said tin halide is stannic bromide, said carboxylic acid is acetic acid and said ester is t-butyl acetate.

* * * * *